United States Patent
Weinstein

(10) Patent No.: US 9,867,816 B2
(45) Date of Patent: *Jan. 16, 2018

(54) PPARγ AGONISTS FOR TREATMENT OF MULTIPLE SCLEROSIS

(71) Applicant: InteKrin Therapeutics, Inc., Los Altos, CA (US)

(72) Inventor: David Weinstein, Los Altos, CA (US)

(73) Assignee: InteKrin Therapeutics, Inc., Redwood City, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 15/402,941

(22) Filed: Jan. 10, 2017

(65) Prior Publication Data

US 2017/0143687 A1 May 25, 2017

Related U.S. Application Data

(63) Continuation of application No. 14/707,122, filed on May 8, 2015, now Pat. No. 9,539,249, which is a continuation-in-part of application No. 14/162,723, filed on Jan. 23, 2014, now Pat. No. 9,061,020.

(60) Provisional application No. 61/758,641, filed on Jan. 30, 2013.

(51) Int. Cl.
*A61K 31/47* (2006.01)

(52) U.S. Cl.
CPC .................... *A61K 31/47* (2013.01)

(58) Field of Classification Search
CPC ..................................... A61K 31/47
USPC ........................................ 514/312
See application file for complete search history.

(56) References Cited

U.S. PATENT DOCUMENTS

| 7,601,841 | B2 | 10/2009 | McGee et al. |
| 9,061,020 | B2 * | 6/2015 | Weinstein ............... A61K 31/47 |
| 2010/0087481 | A1 | 4/2010 | Lee |
| 2010/0184783 | A1 | 7/2010 | Raud et al. |
| 2011/0112097 | A1 | 5/2011 | Jaehne et al. |

OTHER PUBLICATIONS

Ballabh, P. et al., The blood-brain barrier: an overview: structure, regulation, and clinical implications, Neurobiol Dis, Jun. 2004, 16(1), 1-13.
Berge, S. M., et al., "Pharmaceutical Salts", Journal of Pharmaceutical Science, 1977, 66, 1-19.
Minagar A. et al., Blood-brain barrier disruption in multiple sclerosis, Multi Scler, Dec. 2003, 9(6), 540-549.
Tourdias T. et al., Neuroinflammatory imaging biomarkers: relevance to multiple sclerosis and its therapy, Neurotherapeutics, Jan. 2013, 10(1), 111-123.
Bastianello S. et al., Serial study of gadolinium-DTPA MRI enhancement in multiple sclerosis, Neurology, Apr. 1990, 40(4), 591-595.
Smith ME, et al., Clinical worsening in multiple sclerosis is associated with increased frequency and area of gadopentetate dimeglumine-enhancing magnetic resonance imaging lesions, Ann Neural, May 1993, 33(5), 480-489.
Correale J, et al., The blood-brain barrier in multiple sclerosis: functional roles and therapeutic targeting. Autoimmunity, Mar. 2007, 40(2), 148-160.
Lee DH, et al., Selective PPARγ modulator INT131 normalizes insulin signaling defects and improves bone mass in diet-induced obese mice, Am J Physiol Endocrinol Metab, Mar. 1, 2012, 302(5), E552-560.
Feghali CA, et al., Cytokines in acute and chronic inflammation, Front Biosci (Landmark Ed), Jan. 1, 2, 1997, d12-26.
Strum JC, et al., Rosiglitazone induces mitochondrial biogenesis in mouse brain, Mar. 2007, 11(1), 45-51.
Kummer MP, et al., PPARs in Alzheimer's disease, PPAR Research, 2008, ID 403896, 1-8.
Libbey JE, et al., Experimental autoimmune encephalomyelitis as a testing paradigm for adjuvants and vaccines, Apr. 12, 2011, 29(17), 3356-3362.
Clarke, H.J. et al., Cross-Species Differential Plasma Protein Binding of MBX-102/JNJ39659100: A Novel PPAR-gamma Agonist, PPAR Res, 2008, 2008:465715, 1-10.
Grommes, C. et al. The PPARγ agonist pioglitazone crosses the blood-brain barrier and reduces tumor growth in a human xenograft model, Cancer Chemother Pharmacol. Apr. 2013, 71(4), 929-36.
Festuccia, WT. et al., Peroxisome proliferator-activated receptor-gamma-mediated positive energy balance in the rat is associated with reduced sympathetic drive to adipose tissues and thyroid status, Endocrinology, May 2008, 149 (5), 2121-30.
Maeshiba, Y. et al., Disposition of the new antidiabetic agent pioglitazone in rats, dogs, and monkeys, Arzneimittelforschung, Jan. 1997, 47(1), 29-35.
International Search Report and Written Opinion for corresponding PCT Application No. PCT/US14/12656 dated May 13, 2014.
Miller, DH et al., Efficacy of six months' therapy with oral rosiglitazone maleate in relapsingremitting multiple sclerosis, 10th Annual Meeting of the Americas Committee for Treatment and Research in Multiple Sclerosis, Sep. 30, 2005, Abstract. Dowloaded Dec. 28, 2015 from http://registration.akm.ch/einsicht.php?XNABSTRACT_ID=13263&XNSPRACHE_ID=2&XNKONGRESS_ID=22&XNMASKEN_ID=900.

* cited by examiner

*Primary Examiner* — Nizal Chandrakumar
(74) *Attorney, Agent, or Firm* — Wood, Phillips, Katz, Clark & Mortimer

(57) ABSTRACT

Methods of treatment of multiple sclerosis (MS) with PPARγ agonists, and in particular with the compound of formula (I) known as INT131:

(I)

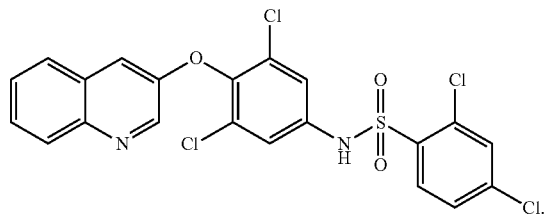

7 Claims, 3 Drawing Sheets
(1 of 3 Drawing Sheet(s) Filed in Color)

PPARγ AGONISTS FOR TREATMENT OF MULTIPLE SCLEROSIS

FIELD OF INVENTION

The present invention relates to methods of treatment of multiple sclerosis ("MS").

BACKGROUND OF THE INVENTION

Multiple sclerosis or MS is a disease that affects the brain and spinal cord resulting in loss of muscle control, vision, balance, sensation (such as numbness) or thinking ability.

In MS, parts of the brain and spinal cord, which together form the central nervous system or CNS are recognized as being foreign and are attacked by one's own immune system. At the cellular level, the CNS is made up by neurons, the "thinking cells" of the nervous system, and glial cells, which perform a wide variety of vital functions. The cell bodies of the neurons are connected to one-another by axons, which function like wires tying neuronal networks together. There are billions of axons in the CNS, which, like copper wires, need to be insulated to prevent loss of signaling, to boost the speed of signaling and to prevent signal interference. The insulating material of the CNS, called myelin, is a specialized organelle of glial cells, which wrap the myelin around the axons. In MS, elements of myelin are recognized as foreign, and are attacked by the individual's own immune system. As a result of these immune attacks the myelin is destroyed, and often, the associated axons are also damaged leading to death. This is an iterative process broken up by periods of remyelination. However, while myelin can reform, eventually the pool of cells that can make myelin is depleted, resulting in areas of chronic CNS demyelination that eventually form scars, also known as plaques, and whose formation is known as sclerosis. When this process of sclerosis is iterative, the resulting form of MS is called relapsing/remitting MS. There is also another rarer form of MS, called primary progressive MS, where no remission occurs. In either case, without the myelin, electrical signals transmitted throughout the brain and spinal cord are disrupted or halted. The affected areas of the brain then become unable to properly send and to receive messages. It is this breakdown of communication that causes the symptoms of MS.

There are a variety of medications available that can reduce the frequency and severity of MS symptoms in some people with MS. Symptoms may be divided into three categories: primary, secondary, and tertiary. Primary symptoms are a direct result of the demyelination process. This impairs the transmission of electrical signals to muscles (to allow them to move appropriately) and the organs of the body (allowing them to perform normal functions.) The symptoms include: weakness, tremors, tingling, numbness, loss of balance, vision impairment, paralysis, and bladder and bowel problems.

Secondary symptoms result from primary symptoms. For example, paralysis (a primary symptom) can lead to bedsores (pressure sores) and bladder or urinary incontinence problems can cause frequent, recurring urinary tract infections. These symptoms can be treated, but the ideal goal is to avail them by treating the primary symptoms.

Tertiary symptoms are the social, psychological, and vocational complications associated with the primary and secondary symptoms. Depression, for example, is a common problem among people with MS.

The course of multiple sclerosis is highly variable. In particular, the earliest stages of the disease can be somewhat unpredictable. Because of this uncertainty, doctors often tell their patients that they "probably" or "possibly" have MS. Diagnosis is based on the combination of clinical presentations, findings on magnetic resonance imaging ("MM") and other tests, and patterns of recurrence. At present there is no way to predict how each person's disease will progress. It often takes an extended period of time before a definitive diagnosis of MS can be made. There are three main courses that MS takes:

Relapsing-remitting MS ("RRMS"): characterized by unpredictable acute attacks, called "exacerbations," with worsening of symptoms followed by full, partial or no recovery of some function. These attacks appear to evolve over several days to weeks. Recovery from an attack takes weeks sometimes months. The disease does not worsen in the periods between the attacks. This pattern usually occurs early in the course of MS in most people.

Primary-progressive MS: characterized by a steady progression of disability, without any obvious relapses and remissions. This form of disease occurs in just 15% of all people with MS, but is more common in people who develop the disease after the age of 40.

Secondary-progressive MS: initially begins with a relapsing-remitting course, but later evolves into progressive disease. The progressive part of the disease may begin shortly after the onset of MS, or it may occur years or decades later.

A true exacerbation of MS is caused by an area of inflammation (i.e. swelling) in the nerves of the brain and spinal cord system followed by something called demyelination, which is the destruction of myelin. The myelin is the fatty sheath that surrounds and protects the nerve fibers. An exacerbation of MS may be mild and not cause a noticeable impairment in functioning or may significantly interfere with a person's daily life. Untreated, exacerbations can last from several days to several weeks, although they may extend into months.

Current therapy intended to slow MS progression has many difficulties. A number of drugs have been shown to slow the progression of MS in some people. These drugs work by suppressing, or altering, the activity of the body's immune system. Thus, these therapies are based on the theory that MS is, at least in part, a result of an abnormal response of the body's immune system that causes it to attack the myelin surrounding nerves. While these disease modifying treatments have altered the natural history of RRMS in many patients, they are non-curative and have significant adverse effects including the sequelae of systemic immunosuppression, as well as fever, body pains, malaise, arthralgia, myalgias, flu-like symptoms, liver function test (LFT) elevations, activation of latent viruses, including John Cunningham (JC) virus, which leads to the oft-lethal Progressive Multifocal Leukoencephalopathy (PML), and more. As a result, the treatments are poorly tolerated by a significant number of patients when given at therapeutic doses and breakthrough disease activity is virtually a given. For the 30% of patients who are either non-responsive, or who have only partial drug-responses (~19%), or for those that do not tolerate therapeutic dosages of otherwise effective drug, there are very limited alternatives. Examples include Avonex® (interferon beta-1a; Avonex is a registered trademark of Biogen Idec MA Inc.), Betaseron® (interferon beta-1b; Betaseron is a registered trademark of Bayer Pharma), Copaxone® (Glatiramer acetate; Copaxone is a registered trademark of Teva Pharmaceutical Industries), Novantrone® (mitoxantrone; Novantrone is a registered trademark of Immunex Corporation), Rebif® (interferon beta-1a; Rebif is a registered trademark of Ares Trading), Tysabri® (natalizumab; Tysabri is a registered trademark of Elan Pharmaceuticals), Tecfidera® (BG12; Tecfidera is a registered trademark of Biogen Idec), Laquinimod™ (Laquinimod is a trademark of Teva Pharmaceuticals) and Aubagio® (Teriflunomide; Aubagio is a registered trademark of Sanofi).

Other undesirable characteristics of these drug therapies include unpleasantness, pain and discomfort associated with injections, leukopenia, opportunistic infections, nausea, vomiting, diarrhea, alopecia, flushing, high cost and drug instability. Accordingly, there is still a need in the art for a safe and effective method for slowing the progression, treatment and alleviating symptoms of MS.

The deterioration of these physical and cognitive functions can also be the result of both neuroinflammation and gray matter loss that is part of the MS neuropathologic process. While immunomodulation and disease modification is partially achieved with the current first-line drugs, they do not provide overall neuroprotection which would be considered the holy grail of therapy.

SUMMARY OF THE INVENTION

It has now been discovered that PPARγ agonists are effective for MS. These compounds are agonists of the peroxisome proliferator-activated receptor γ (PPARγ). The PPARγ is a transcription factor belonging to the steroid/thyroid/retinoid receptor superfamily. To date, PPARγ agonists have been therapeutic agents for disorders such as obesity, diabetes and dyslipidemia.

In one aspect, the present invention provides methods of treating or preventing MS relapses. The methods typically involve administering to a subject in need thereof a therapeutically effective amount of compounds principally described in U.S. Pat. No. 7,601,841 and specifically one referred herein below as INT131. INT131 is unique among PPARγ agonists in that it is a selective activator of a highly limited number of PPARγ pathways. Among these INT131-sensitive pathways are anti-inflammatory and neuroprotective gene activation cascades.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
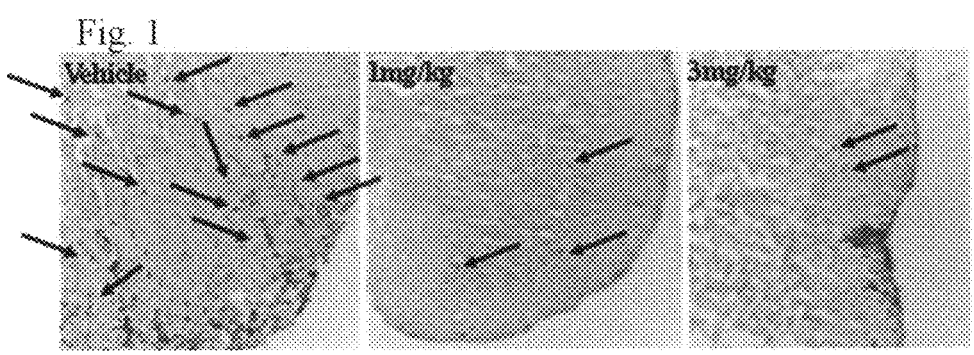
FIG. 1 is a photograph of brainstem cross-sections of INT131 treated and untreated mice with arrows identifying infiltrating CD45-positive leukocytes.

In particular, the compound (I),

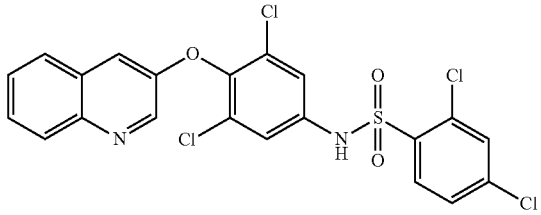 [SMILES: O=S(=O)(Nc1cc(Cl)c(Oc2cnc3ccccc3c2)c(Cl)c1)c1ccc(Cl)cc1Cl]

has been found to be unexpectedly effective for MS. This compound is also known as INT131.

Abbreviations and Definitions

The abbreviations used herein are conventional, unless otherwise defined.

The terms "treat", "treating" and "treatment" refer to a method of alleviating or abrogating a disease and/or its attendant symptoms.

The terms "prevent", "preventing" and "prevention" refer to a method of decreasing the probability or eliminating the possibility that a disease will be contracted.

The term "therapeutically effective amount" refers to that amount of the compound being administered sufficient to prevent development of or alleviate to some extent one or more of the symptoms of the condition or disorder being treated.

The term "subject" is defined herein to include animals such as mammals, including but not limited to, primates (e.g., humans), cows, sheep, goats, horses, dogs, cats, rabbits, rats, mice and the like. In preferred embodiments, the subject is a human.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either net or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either net or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isbutyric, oxalic, maleic, malonic, benzoic, succinic, suberic, fumeric mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science,* 1977, 66, 1-19). Certain specific compounds of the present inventions contain both basic and acidic functionalities that allow the compounds to be converted into either base or acid addition salts.

The neutral forms of the compounds may be registered by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In additional to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Embodiments of the Invention

A new use of known compounds that modulate PPARγ has now been discovered.

The experimental autoimmune encephalomyelitis ("EAE") model has been shown to be a valid and accurate predictor of the effects of a compound of treatment paradigm on MS in humans. As seen below, treatment with INT131 of animals with EAE with INT131, results in the subjects becoming and remaining mostly symptom-free. Accordingly, it is believed that INT131 will be effective for the treatment of MS.

In particular, the compound (I),

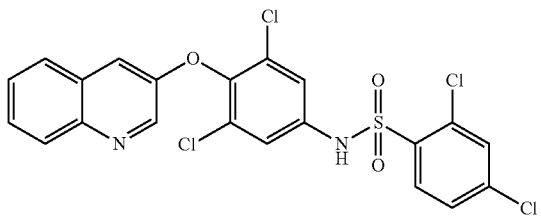

has been found to be unexpectedly effective for MS. This compound is also known as INT131.
We anticipate that 1-3 mg/day is likely to be a sufficient dose to elicit the desired response.

Example 1

INT131 is a Potent Inhibitor of EAE Progression
INT131 Reduces Relapse in Mouse Model EAE is a well-characterized and widely used model of MS. It is one of the few animal models in which drug therapeutic activity in the model often mimics and anticipates the drug's effects in human disease. In this model, mice are immunized with well-defined antigenic fragments of central nervous system myelin, such as fragments of the proteolipid protein (PLP). Over the course of 2 to 3 weeks the immunized animals develop a clinical and histopathologic syndrome of T-cell mediated cerebral autoimmunity that is highly reminiscent of relapsing/remitting MS (RRMS). The similarities between EAE and RRMS include inflammatory cerebral infiltrated and accompanying Th1/Th17 responses to both the disease initiating myelin PLP peptide, and subsequent epitope spread, seen in disease relapse.

The animals were immunized with the myelin peptide ($PLP^{139-151}$) and the spread epitope peptide ($PLP^{178-191}$) which drives disease relapse. Studies consisted of three experimental arms in which the mice were given daily ip injection of vehicle, or either 1 or 3 mg/kg/d of INT131. Following immunization, the animals underwent daily neurological evaluation by an experienced investigator. In these studies treatment began at the time of the first remission.

INT131 treatment virtually blocks relapse. Following the expected clinical disease peak at about two weeks post-immunization, symptoms began to ebb as the animals drifted into remission. All of the animals were treated with INT131 on day 20. By the $22^{nd}$ day following immunization relapse began as expected, however, only in the vehicle treated animals. In contrast, the INT131 treated mice either continued to improve slightly (1 mg/kg), or remained stable (3 mg/kg).

A comparison of relapse rate on the $25^{th}$ day post-immunization demonstrated a highly significant reduction in the relapse in both INT131 treatment paradigms, as compared to the vehicle-treated subjects. Between 9 percent (1 mg/kg/d) and 16 percent (3 mg/kg/d) of the INT131-treated animals relapsed, as compared to 72 percent of the vehicle-treated mice. Among the INT131-treated animals that do relapse, the disease burden is exceptionally mild in comparison to the vehicle treated mice.

INT131 Mediates Leukocyte Clearance from the CNS

Figure 2:
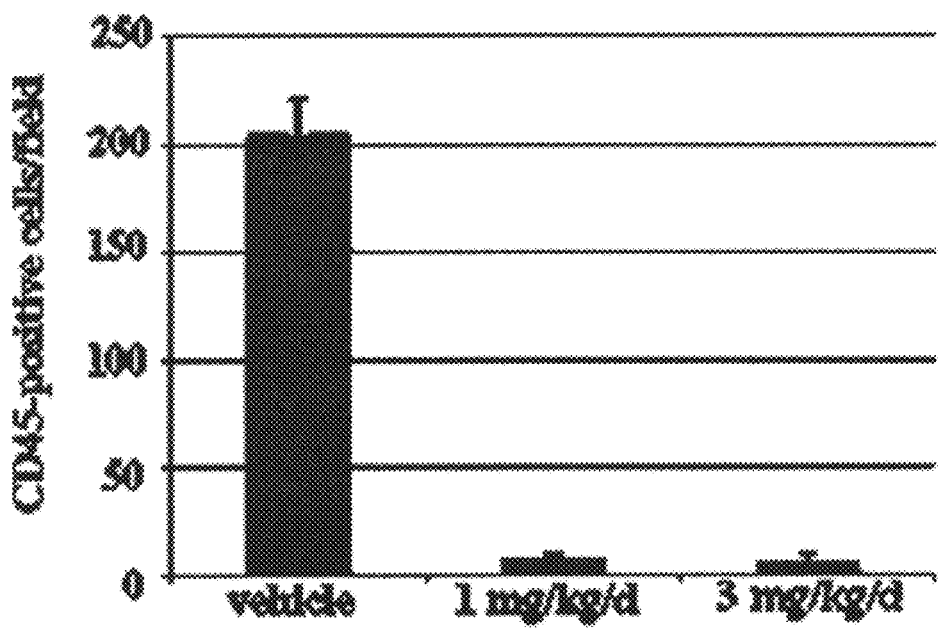
FIG. 2 is a graphical representation of the number of infiltrating CD45-positive leukocytes found in the brainstem of INT131 treated and untreated mice.

Initiating INT131 treatment during remission extends the time subjects remain relapse-free, as compared to vehicle/placebo treatment. However, because there is little active neuroinflammation during remission, this paradigm is not informative about the effects of INT131 on acute neuroinflammation. To better understand the effects of INT131 on the acute inflammatory response we treated mice with EAE at the height of the clinical disease. As discussed above, this results in a rapid improvement in clinical symptoms. Examination of neural tissue from mice treated with INT131 at the peak of disease demonstrates a paucity of infiltrating CD45-positive leukocytes in the INT131 treated tissue, compared to an exuberant leukocyte infiltration observed in neural tissue from the vehicle-treated animals (FIGS. 1 and 2).

INT131 treatment was begun at the peak of disease (day 20) and brainstems were harvested at day 32, and stained with αCD45 to identify infiltrating leukocytes. CD45 (also known as Leukocyte Common Antigen) is expressed on all hematopoietic cells except erythrocytes and platelets, and is required for B- and T cell-receptor-mediated activation. Thus, CD45 is critical in mediating the inflammatory process. As seen in FIG. 1, there are numerous CD45-expressing cells in the tissue from the vehicle-treated subjects (arrows), while there are few in either concentration of INT131-treated tissue. Quantitation of the number of CD45-positive leukocytes in the brain stems of animals treated with INT131 at the peak of disease shows that drug treatment results in a paucity of infiltrating white cells 12 days after treatment initiation (FIG. 2). These findings unify the clinical and histological findings that INT131 is a potent and effective treatment of acute neuroinflammation in this model of RRMS.

Example 2

Bioavailability in the Central Nervous System

Background

The Blood Brain Barrier ("BBB") is a physical/biochemical impediment that acts as a diffusion barrier and a physical sieve to impede the influx of most macromolecules and blood-borne cells from entering the brain. The BBB is formed by the physical interactions of the three distinct cellular components that comprise it, including endothelial cells, astrocyte end-feet, and pericytes. The diffusion barrier function of the BBB is dependent upon tight junctions that form between the cerebral endothelial cells, which selectively exclude most blood-borne substances from entering the brain. Ballabh, P. et al., The blood-brain barrier: an overview: structure, regulation, and clinical implications, *Neurobiol Dis,* 2004, June, 16(1), 1-13. In the setting of acute inflammation, as occurs during MS relapse, the BBB near the lesion breaks down, allowing the influx of both immunomodulatory macromolecules and leukocytes to the lesion site, which further drives the inflammatory process forward. Minagar A. et al., Blood-brain barrier disruption in multiple sclerosis, *Multi Scler,* 2003, December, 9(6), 540-549.

The acute inflammatory lesions in MS can be detected in real-time with the use of contrast-enhanced MRI. Under normal homeostatic conditions, the BBB prevents the passage of gadolinium-based contrast medium into the brain and spinal cord. However, at the sites of acute inflammation, the BBB is impaired, and gadolinium readily enters the lesion, where it is seen as a bright area in the MR image. Tourdias T. et al., Neuroinflammatory imaging biomarkers: relevance to multiple sclerosis and its therapy, *Neurotherapeutics,* 2013, January, 10(1), 111-123. However, this process is short lived, with about 70% of the lesions excluding gadolinium within 30 days, owing to the reformation of the local BBB. Bastianello S. et al., Serial study of gadolinium-DTPA MRI enhancement in multiple sclerosis, *Neurology,* 1990, April, 40(4), 591-595; Smith M E, et al., Clinical worsening in multiple sclerosis is associated with increased frequency and area of gadopentetate dimeglumine-enhancing magnetic resonance imaging lesions, *Ann Neurol,* 1993, May, 33(5), 480-489. Therefore, if therapeutic compounds are to be effective over the full course of RRMS, including the extended periods of remission, it is critical that a compound be able to cross the intact BBB that is restored during remission. Correale J, et al., The blood-brain barrier in multiple sclerosis: functional roles and therapeutic targeting. *Autoimmunity,* 2007, March, 40(2), 148-160.

Procedure

To test whether INT131 is able to penetrate the intact BBB INT131 was radiolabeled with tritium ("[$^3$H] INT131"), prior to intraperitoneal injection into adult Sprague-Dawley rats. The purity of the radiolabeled INT131 was determined by high-performance liquid chromatography (HPLC) fractionation prior to injection, and again at the close of the experiment. At both time points virtually all of the radiolabeled material was found in a single peak, demonstrating the stability of [$^3$H]INT131 over the course of the study. At the time of injection into the test animals, the labeled INT131 was mixed with non-labeled INT131 such that the injection of 50 mg/kg of INT131 resulted in each animal receiving 1000 µCi/kg of labeled drug. The test animals were sacrificed at 1, 6 and 24 hours after injection and blood, brain, cerebrospinal fluid ("CSF"), spinal cord, kidney, liver and small bowel were harvested for determination of [$^3$H]INT131 content by liquid scintillography.

Results

Table 1 lists the INT131 concentration in all the tissues analyzed. One hour after a single administration of ~50 mg/kg of [$^3$H]INT131, the average amount of INT131 in the neural compartments was less than 0.5 µg/gram of brain tissue, which was approximately 10 fold less than that found in the circulation. In contrast, at 6 and 24 hours, the amount of INT131 in the neural tissues had increased approximately 10 fold. This delay in accumulation of drug in neural tissues is consistent with its active transport across the BBB.

Figure 3:
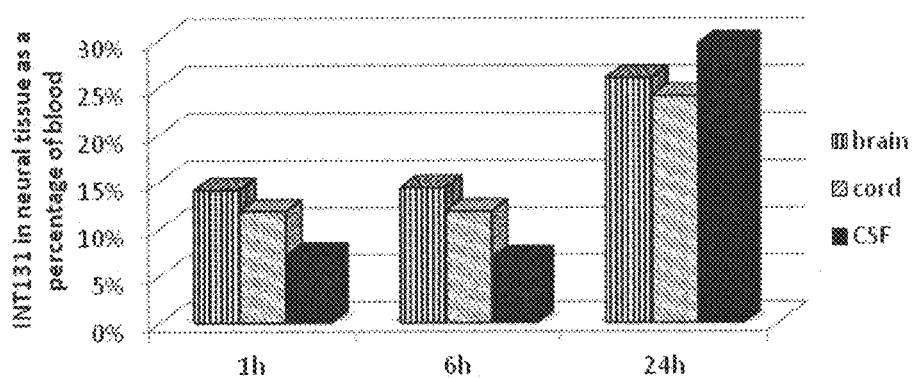
FIG. 3 is a graphical representation of the bioavailability of INT131 in the brain, spinal cord and CSF, relative to its bioavailability in blood.

The bioavailability of INT131 in the brain and spinal cord increased over the course of 24 hours such that it was ~10% the level found in blood 6 hours after injection, whereas by 24 hours, the level of INT131 in neural tissues had increased to 25% of that found in the circulation (FIG. 3). The absolute amount of INT131 in the brain and spinal cord 1 day after injection was over 4 µg/gram of wet neural tissue (see Table 1). This is an amount of drug that is more than sufficient to saturate the available PPARγ receptor. Lee D H, et al., Selective PPARγ modulator INT131 normalizes insulin signaling defects and improves bone mass in diet-induced obese mice, *Am J Physiol Endocrinol Metab,* 2012 Mar. 1, 302(5), E552-560. Separate analysis of the brain and spinal cord, which together form the central nervous system, showed similar accumulation of labeled INT131 at each time point analyzed, thereby serving as an internal control on both the assay and the true distribution of the drug. The timing and high levels of compound found in liver and gut are likely the result of the known routes of INT131 metabolism and excretion.

As shown in FIG. 3 and Table 1, there is a lag in the accumulation of drug in the CSF, relative to the brain and spinal cord, between 6 and 24 hours. This finding is consistent with the known biology of the BBB. The solutes present in the CSF accumulate through active transport of the drug from the choroid plexus to CSF, a relatively slow process. The delay in INT131 accumulation in the CSF, compared to the brain and spinal cord, further supports the conclusion of INT131 penetration of the blood-brain barrier.

TABLE 1

Distribution of INT131 in tissues at 1, 6 and 24 hours after administration.

| | μg/gram wet weight | | |
|---|---|---|---|
| | 1 h | 6 h | 24 h |
| Blood | 4.048 | 41.804 | 17.939 |
| Brain | 0.569 | 5.976 | 4.646 |
| CSF | 0.292 | 2.862 | 5.298 |
| Spinal cord | 0.478 | 4.814 | 4.306 |
| Kidney | 7.732 | 32.851 | 15.429 |
| Liver | 24.393 | 140.84 | 36.36 |
| Small bowel | 19.711 | 222.98 | 34.456 |

Example 3

Neuroprotection

Cortical and subcortical gray matter atrophy are seen in all stages of MS, however, thalamic loss has recently emerged as a sensitive and reliable marker of MS progression in the early stages of the disease. It is expected that the addition of INT131 at either 1 or 3 mg will result in sparing of thalamus from additional atrophy. INT131 would then be the first drug that clinically has demonstrated against gray matter atrophy in MS.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the description there have been disclosed exemplary embodiments and, although specific terms may have been employed, they are unless otherwise stated used in a generic and descriptive sense only and not for purposes of limitation, the scope of the claims therefore not being so limited.

Moreover, one skilled in the art will appreciate that certain steps of the methods discussed herein may be sequenced in alternative order or steps may be combined. Therefore, it is intended that the appended claims not be limited to the particular embodiment disclosed herein.

What is claimed is:

1. A method of treating grey matter atrophy in a patient in need thereof comprising administering to said patient at regular dosing intervals a pharmaceutical composition comprising a therapeutically effective amount of a compound of formula (I),

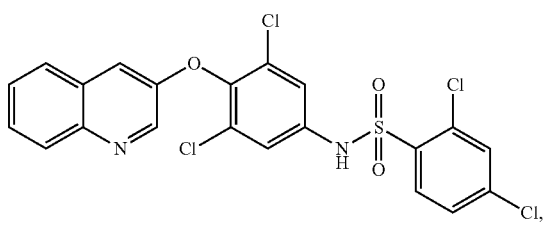

or a pharmaceutically acceptable salt thereof.

2. The method of claim 1, wherein the regular dosing interval is once per day.

3. The method of claim 1, wherein the therapeutically effective amount of the compound of formula (I) is from about 1 to about 3 milligrams.

4. The method of claim 3, wherein the amount of the compound of formula (I) is about 1 milligrams per day or about 3 milligrams.

5. The method of claim 4, wherein the amount of the compound of formula (I) is about 1 milligrams.

6. The method of claim 4, wherein the amount of the compound of formula (I) is about 3 milligrams.

7. The method of claim 1, wherein the regular dosing interval is once per day and the therapeutically effective amount of the compound of formula (I) is from about 1 to about 3 milligrams.

* * * * *